United States Patent
Tatsuno et al.

[11] Patent Number: 6,030,339
[45] Date of Patent: Feb. 29, 2000

[54] IMAGING ASSEMBLY FOR ENDOSCOPES MAKING IT POSSIBLE TO DETACHABLY ATTACH UNITS THEREOF, IN WHICH ELECTRIC OPTICAL SYSTEM AND IMAGING DEVICE ARE INCORPORATED RESPECTIVELY, TO EACH OTHER AND TO AUTOCLAVE THEM

[75] Inventors: Yutaka Tatsuno, Sagamihara; Fuminori Tanahashi, Hachioji, both of Japan

[73] Assignee: Olympus Optical Co., Ltd., Japan

[21] Appl. No.: 09/119,316

[22] Filed: Jul. 20, 1998

[51] Int. Cl.[7] ............................................. A61B 1/04
[52] U.S. Cl. ............................................. 600/112; 600/133
[58] Field of Search ........................ 600/112, 110, 600/133, 109

[56] References Cited

U.S. PATENT DOCUMENTS

| | | | |
|---|---|---|---|
| 4,574,783 | 3/1986 | Kazuhiro | 600/133 |
| 4,611,888 | 9/1986 | Prenovitz | 600/133 |
| 5,056,902 | 10/1991 | Chinnock et al. . | |
| 5,156,141 | 10/1992 | Krebs | 600/112 |
| 5,188,094 | 2/1993 | Adair | 600/133 |
| 5,349,137 | 9/1994 | Cedrone | 600/133 |
| 5,349,941 | 9/1994 | Hori | 600/133 |
| 5,359,992 | 11/1994 | Hori et al. . | |
| 5,498,230 | 3/1996 | Adair | 600/112 |
| 5,536,244 | 7/1996 | Muller | 600/133 |
| 5,591,119 | 1/1997 | Adair | 600/112 |
| 5,609,561 | 3/1997 | Uehara | 600/133 |
| 5,611,769 | 3/1997 | Monroe | 600/112 |
| 5,868,664 | 2/1999 | Speier | 600/112 |
| 5,876,327 | 3/1999 | Tsuyuki | 600/112 |
| 5,879,285 | 3/1999 | Ishii | 600/110 |

FOREIGN PATENT DOCUMENTS

| | | |
|---|---|---|
| 6-138397 | 5/1994 | Japan . |
| 7-49458 | 2/1995 | Japan . |

*Primary Examiner*—John P. Leubecker
*Attorney, Agent, or Firm*—Ostrolenk, Faber, Gerb & Soffen, LLP

[57] ABSTRACT

An electric optical adapter unit that is freely detachably attached to a rigid endoscope has an optical system stowed in the center of a housing thereof. An electric circuit such as an automatic iris unit is stowed on the circumference of the optical system. Openings of a frame at both ends of the optical system are sealed hermetically with cover glasses so that the optical system can withstand autoclaving. Electric contact pins fixed in annular plug are hermetically sealed with glass hermetic seals in the back end surface of the frame. In a TV camera unit connected to the back end of the electric optical adapter unit, a CCD and the like are stowed in the center of an imaging optical system housing that is sealed hermetically. A receptacle structured to be watertight is mounted on the circumference of the imaging optical system housing. The receptacle can be freely detachably attached to the electric contact pins of the annular plug, whereby an electric signal can be transmitted.

16 Claims, 8 Drawing Sheets

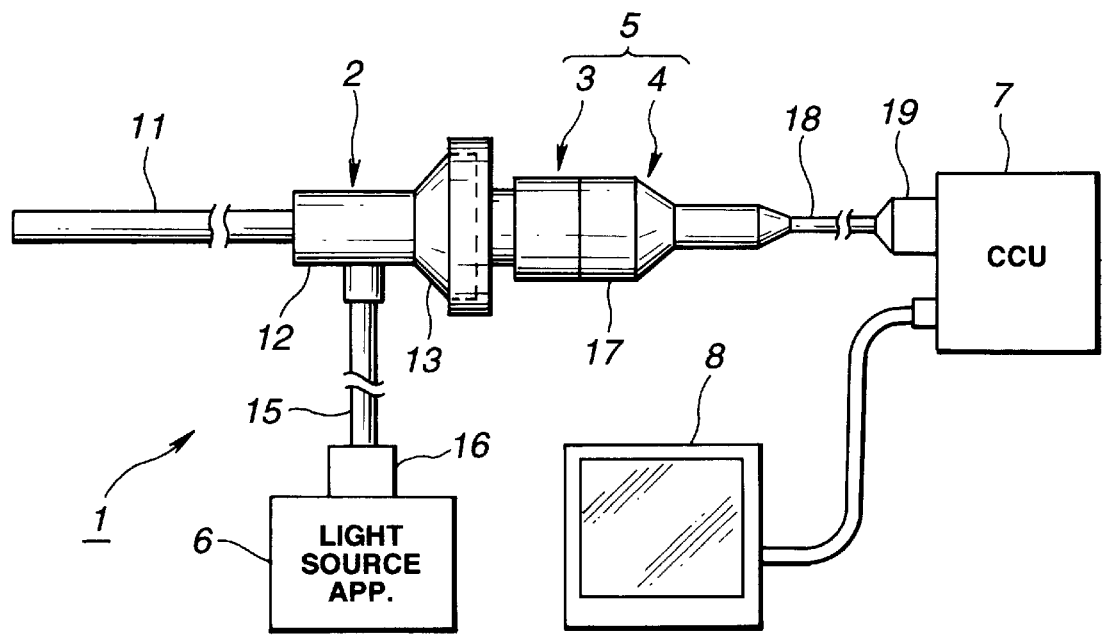
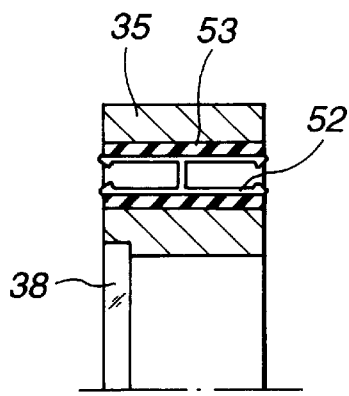 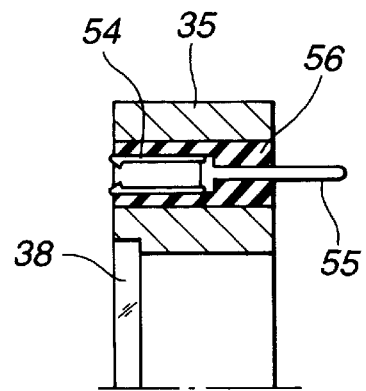

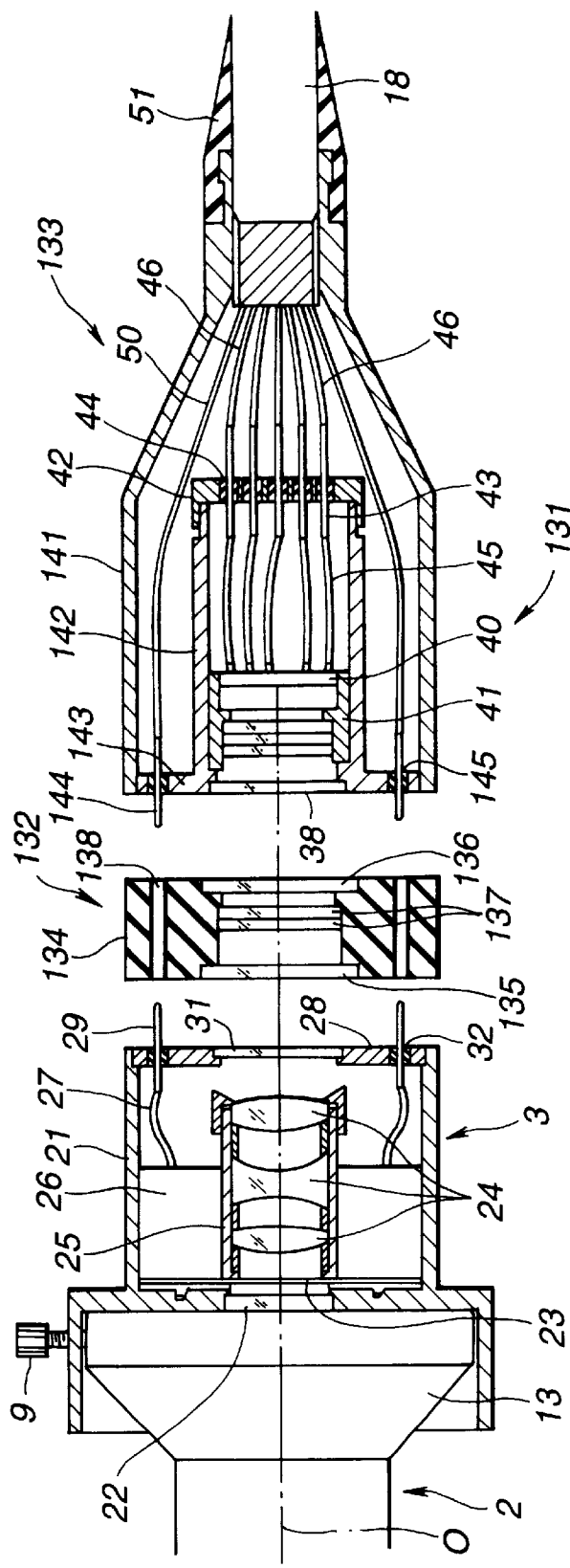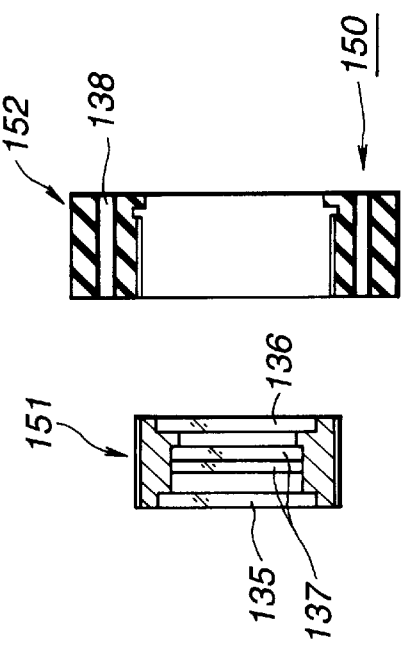

IMAGING ASSEMBLY FOR ENDOSCOPES MAKING IT POSSIBLE TO DETACHABLY ATTACH UNITS THEREOF, IN WHICH ELECTRIC OPTICAL SYSTEM AND IMAGING DEVICE ARE INCORPORATED RESPECTIVELY, TO EACH OTHER AND TO AUTOCLAVE THEM

BACKGROUND OF THE INVENTION

1. Field of the Invention

The present invention relates to an imaging assembly for endoscopes making it possible to detachably attach a first unit which is attached to an endoscope and includes an electric optical system or the like, to a second unit in which an imaging device is incorporated, and to autoclave them.

2. Description of the Related Art

In recent years, an optical adapter having an electric circuit, such as an automatic iris mechanism has been utilized. Autoclaving using high-temperature and high-pressure steam which does not impair an environment has been adopted as a sterilizing method. High-level airtightness that provides higher durability than airtightness attained generally under 1 atm or watertightness during disinfection using known chemicals has come to be requested.

For example, Japanese Unexamined Patent Publication No. 7-49458 has disclosed an imaging assembly for endoscopes having a photographic lens unit which is freely detachably attached to an endoscope and a camera head in which an imaging device is incorporated, wherein the photographic lens unit and the camera head are freely detachably attached to each other.

The above patent publication describes a structure capable of being autoclaved by including a photographic lens and electric diaphragm in a photographic lens unit. The patent publication has disclosed neither a practical connector structure by which electric contacts are detachably attached for linkage of signal lines coupled to the electric diaphragm, nor a practical structure actually enabling autoclaving.

In the imaging assembly for endoscopes of the prior art, a watertight connector sealed with a resin is conventionally formed with the electrical contacts. However, this structure cannot ensure fully hermetic sealing against high-pressure steam dissipated during autoclaving.

In general, a connector used for a hermetically sealed body that undergoes a high-pressure gas is of a glass hermetic type. However, a hermetic connector is shaped like a solid plan and therefore hard to be structured so that portions of an optical system can be separated from each other.

According to the prior art, therefore, an optical adapter including an electrical circuit and a camera head are united with each other. It is therefore impossible to select any optical adapter which performs in the same manner as an exchange lens for a camera. The imaging assembly for endoscopes has drawbacks in that it is hard to expand capability and an economic load incurred by a user is large.

Incidentally, U.S. Pat. Nos. 5,056,902 and 5,359,992 have disclosed assemblies in which an adapter to be connected to an endoscope has a hermetic structure, and a stowed lens can be focused by utilizing magnetic force.

These prior arts provide structures not including an electrical system.

SUMMARY OF THE INVENTION

An object of the present invention is to provide an imaging assembly for endoscopes making it possible to separate an optical adapter which includes an electrical circuit and a camera head which has an imaging device incorporated therein, from each other to autoclave them.

Another object of the present invention is to provide an imaging assembly for endoscopes making it possible to separate an optical adapter which includes an electrical circuit and a camera head which has an imaging device incorporated therein, from each other to autoclave them, and which is capable of being designed compactly.

An imaging assembly for endoscopes comprises:

a first unit freely detachably attached to an eyepiece unit of an optical endoscope and having an optical system located inside a first optical device used to hermetically seal one opening of a first housing opposed to an optical device of the eyepiece unit, and additionally having an electrical circuit which generates an electrical signal used for driving or the like, and is hermetically stowed in the first housing so that the optical system and electrical circuit can withstand autoclaving where high-temperature and high-pressure steam is used for sterilization;

a second unit having an imaging unit which includes a solid-state imaging device stowed in a second housing for photoelectrically converting an optical image formed through the optical system, and having an opening opposed to the optical system and is hermetically sealed with a second optical device, so that the imaging unit can withstand autoclaving;

a separable connection member for connecting the first and second units so that they can be separated from each other;

a third optical device facing the separable connection member and hermetically sealing the other opening of the first housing case opposed to the optical system;

a first electrical connector having first electrical contacts coupled to the electrical circuit which is hermetically sealed with hermetic seals on the circumference of the other opening of the first housing so that the first electrical contacts can withstand autoclaving; and a second electrical connector formed in the second housing facing the separable connection member and having second electrical contacts which are freely detachably attached to the first electrical contacts of the first electrical connector and having a waterproof structure.

The first unit and second unit can be separated from each other and autoclaved. During autoclaving, the optical system and imaging device are sealed hermetically. Consequently, clouding of the optical system or degrading of the characteristics of the imaging device can be prevented. Moreover, since the first unit and second unit can be separated from each other, the first unit or second unit can be used in combination with any unit exhibiting different characteristics. This permits expansion of the capability of the imaging assembly for endoscopes.

BRIEF DESCRIPTION OF THE DRAWINGS

FIGS. 1 to 4B relate to the first embodiment of the present invention;

FIG. 1 is a diagram showing an overall configuration of an endoscope system including the first embodiment;

FIG. 2 is a sectional view showing a practical structure of an imaging assembly for endoscopes in accordance with the first embodiment;

FIG. 3 is a diagram showing a structure of a back end surface of an electric optical adapter unit seen in the direction of an arrow A in FIG. 2;

FIGS. 4A and 4B are sectional views showing structures of variants of a receptacle of a TV camera unit;

FIG. 10 is a sectional view showing a structure of an imaging assembly for endoscopes in accordance with the seventh embodiment of the present invention;

FIG. 11 is a sectional view showing a structure of a filter unit in a variant of the seventh embodiment;

FIG. 12 is a sectional view showing a structure of an imaging assembly for endoscopes in accordance with the eighth embodiment;

FIG. 13 is a diagram showing an electrically coupled state of opposed contact pins with a connection ring and mount attached to each other.

DESCRIPTION OF THE PREFERRED EMBODIMENTS

Figure 2:
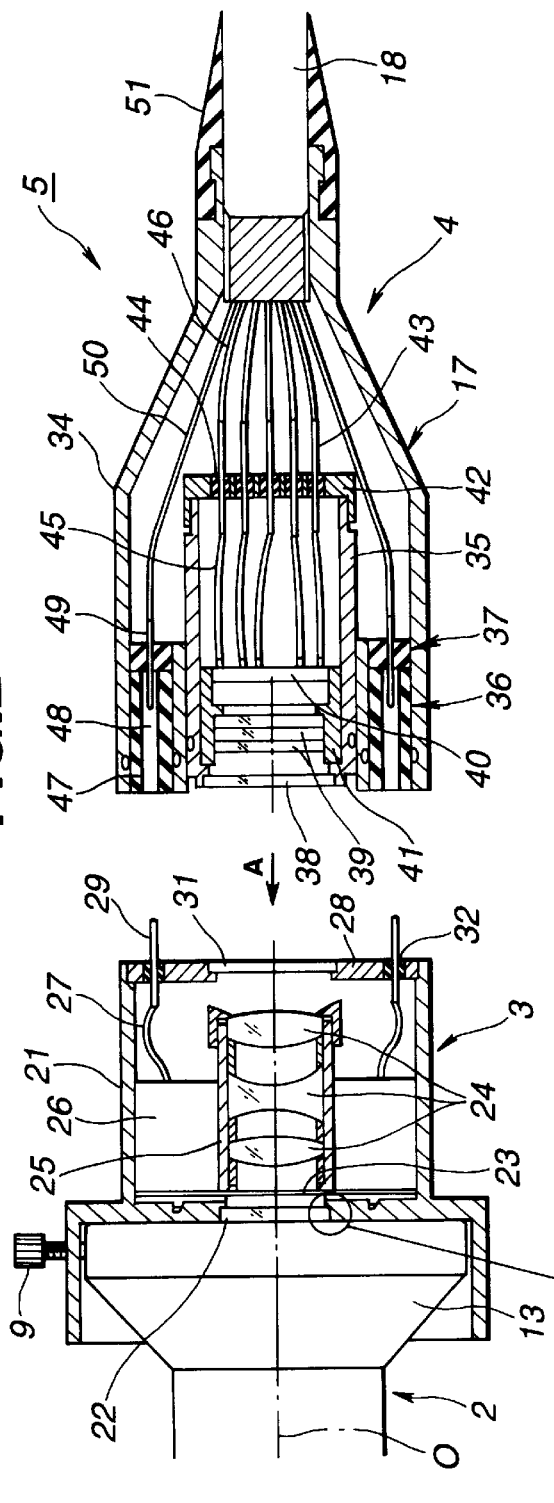

The first embodiment of the present invention will be described with reference to FIGS. 1 to 4.

As shown in FIG. 1, an endoscope system 1 comprises: an optical endoscope or more particularly a rigid endoscope 2; an imaging assembly for endoscopes 5 composed of an electric optical adapter unit 3 serving as a first unit which can be freely detachably attached to the rigid endoscope 2 and includes an electrical circuit and optical system, and a TV camera unit 4 that is freely detachably attached to the electric optical adapter unit 3 and serves as a second unit which has an imaging device incorporated therein; a light source apparatus 6 for supplying illumination light to the rigid endoscope 2; a camera control unit (CCU) 7 for processing signals sent from the imaging assembly for endoscopes 5; and a monitor 8 for displaying a video signal output from the CCU 7.

The rigid endoscope 2 includes an insertion unit 11 that is elongated and rigid, a large-diameter hand-held unit 12 formed at the back end of the insertion unit 11, an eyepiece unit 13 formed at the back end of the hand-held unit 12, and a base formed on a lateral side of the hand-held unit 12. A light guide cable 15 is coupled to the base. A connector 16 is spliced to the terminal of the light guide cable 15 can be freely detachably attached to the light source apparatus 6.

When the connector 16 of the light guide cable 15 is attached to the light source apparatus 6, white light emanating from a lamp, which is not shown, in the light source apparatus 6 is irradiated to the end surface of the light guide. Illumination light propagated through the light guide is supplied to a light guide lying through the rigid endoscope 2, and emitted forward through an illumination window in a distal part of the insertion unit 11. Consequently, an object is illuminated.

An image of the object illuminated with the illumination light emitted through the illumination window is formed by an objective lens, which is not shown, located in the distal part. The formed image is transmitted to an eyepiece unit 13 by a relay optical system, and viewed in enlargement through an eyepiece lens.

A camera head 17 of the TV camera unit 4 is freely detachably attached to the eyepiece unit 13 via the electric optical adapter unit 3. A connector 19 spliced to an end of the camera cable 18 extending from the camera head 17 can be freely detachably attached to the CCU 7.

As shown in FIG. 2, the electric optical adapter unit 3 has a system of image formation lenses 24 located in the center thereof opposed to an eyepiece lens, which is not shown, of the eyepiece unit 13. An optical image is then formed on the CCD 40 incorporated in the TV camera unit 4 attached to the electric optical adapter unit 3.

A CCD driving signal is applied from the CCU 7 to the CCD 40 over a signal line in the camera cable 18. This triggers photoelectric conversion. An image signal is then read, and input to a video signal generator, which is not shown, in the CCU 7. A video signal is then generated. An optical image is then displayed on the display surface of the monitor 8.

Moreover, a driving signal for light adjustment which indicates an average level of brightness is generated using a luminance signal generated in the CCU 7. The driving signal is transmitted to the TV camera unit 4 over the signal line in the camera cable 18, and input to an iris drive unit 26 in the electrical optical adapter unit 3 over a signal line in the TV camera unit 4. An opening diameter of aperture blades 23 in the electric optical adapter unit 3 is varied in order to adjust an amount of incident light. Thus, light is automatically adjusted so that an object image having proper brightness can be produced.

The structure of the imaging assembly for endoscopes 5 in accordance with the first embodiment, which consists of the electric optical adapter unit 3 and TV camera unit 4 shown in FIG. 2, will be described specifically.

As shown in FIG. 2, a mount is located at the front end of the adapter housing 21 that outlines the electric optical adapter unit 3 of this embodiment and is shaped substantially like a cylinder. The mount is engaged with and freely detachably attached to the eyepiece unit 13 by means of a set screw 9. An optical device, or more specifically a first cover glass 22 that is shaped like a disk, has an outer circumference thereof metallized with a metallic coat 22a. The first cover glass 22 is locked in an opening of the adapter housing 21 that is opposed to an eyepiece window, which is not shown, for the eyepiece unit 13 along an optical axis O. The first cover glass 22 is hermetically fixed to the metallic adapter housing 21 by fusing high-temperature solder or wax 10. Thus, the metallic adapter housing 21 is sealed hermetically to permit sterilization with high-temperature and high-pressure steam, that is, to permit and withstand autoclaving.

Due to the hermetic structure permitting autoclaving, a hermetic state can be retained during autoclaving in which an object to be sterilized is exposed to steam or a temperature ranging from 121 to 135° C. at a pressure ranging from 1.5 to 2.2 atm.

A lens frame 25 having the aperture blades 23 and system of image formation lenses 24 stowed therein is placed in the adapter housing hermetically sealed with the first cover glass 22 so that the center line thereof will be aligned with the optical axis O.

Moreover, the annular iris drive unit 26 is mounted on the outer circumference of the lens frame 25 in the adapter housing 21. An opening diameter of the aperture blades 23 can be varied by applying a driving signal to a drive motor, which is not shown, in the iris drive unit 26. This enables adjustment of an amount of light incident on the system of image formation lenses 24.

An end of an iris driving harness 27 serving as a signal line is coupled to the iris drive unit 26. The other end of the iris driving harness 27 is joined with a contact pin 29 locked in a first plug 28 fixed hermetically to the back end of the adapter housing 21.

The first plug 28 is a metallic disk-like member closely fitted in a circular opening at the back end of the adapter housing 21, and is hermetically sealed to permit autoclaving.

Moreover, a circular opening whose center is aligned with the optical axis O of the system of image formation lenses 24 is formed in the center of the first plug 28. A second cover glass 31 is hermetically locked in the opening (in the same manner as the first cover glass 22) in order to permit successful autoclaving. Thus, an optical path is defined.

Figure 3:
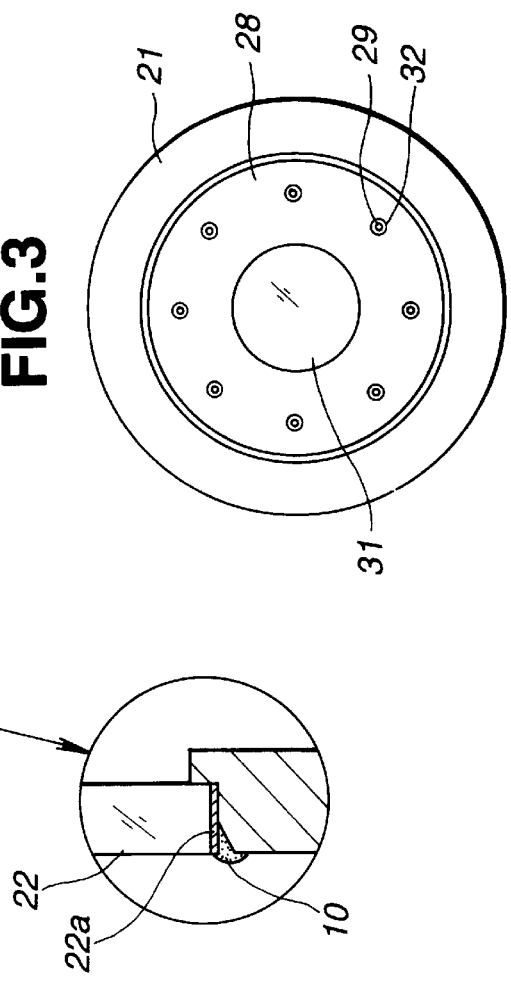

The first plug 28, as shown in FIG. 3 which shows the adapter unit 3 in the direction of an arrow A in FIG. 2, is shaped like a ring (annular). An optical device, more specifically the second cover glass 31, is locked hermetically in the circular opening in the center of the first plug 28. A plurality of contact pins 29 is locked in the annular first plug 28 coaxial with the second cover glass 31 by means of glass hermetic seals 32.

In other words the contact pins 29 are penetrated throughholes having a larger diameter than the contact pins. Fused glass is poured into the annular spaces in the holes, thus sealing the pins hermetically. This results in the glass hermetic seals 32 realizing a hermetically sealed structure that permits autoclaving.

As mentioned above, the center of the adapter housing is designed as the optical path and is surrounded by the contact pins 29. This results in the small outer diameter of the optical adapter unit 3.

In contrast, a camera housing 34 outlining the camera head 17 is shaped like a cylinder having the back portion thereof tapered. An imaging optical system housing 35 is placed in the center of the camera housing. A receptacle 36 and a second plug 37, both of which are annular, are mounted on the outer circumference of the imaging optical system housing 35.

The imaging optical system housing 35 is made of a metal and shaped like a cylinder. An optical device, more specifically a third cover glass 38, is hermetically locked in a circular opening at the front end of the imaging optical system housing so that the imaging optical system housing 35 can be autoclaved. An optical filter 39 and a chargecoupled device (CCD) 40, together serving as a solid-state imaging device, are sealed in the imaging optical system housing 35 with a device frame 41 between them.

Moreover, a third plug 42 that is metallic is fitted hermetically in an opening at the back end of the imaging optical system housing 35. Contact pins 43 are fitted into the third plug 42 by means of glass hermetic seals 44 in such a way that the contact pins extend inside and outside the third plug 42. This results in a hermetically sealed structure permitting autoclaving.

In the imaging optical system housing 35, the contact pins 43 are linked to leads formed on the back surface of the CCD 40 by signal transmission harnesses 45. Outside the imaging optical system housing 35, the contact pins 43 are joined with signal transmission harnesses 46 constituting the camera cable 18.

The annular receptacle 36 is mounted on the outer circumference of the front-end portion of the imaging optical system housing 35 via a cylindrical member. The receptacle 36 is formed by boring through-holes at positions in an annular insulating member 47 at which the through-holes are opposed to the contact pins 29, and then affixing cylindrical contact sockets 48 in the through-holes. The contact pins 29 can be inserted into the contact pin insertion holes on the front sides of the contact sockets 48. Contact pins 49 thrust through the second plug 37 are inserted into the contact pin insertion holes on the back sides thereof. The second plug 37 is formed with an insulating member in which the contact pins 49 are locked therethrough.

An O-ring useful for attaining watertightness is interposed between the outer circumference of the imaging optical system housing 35 and the inner circumference of the cylindrical member, between the outer circumference of the insulating member 47 and the inner circumference thereof, and between the outer circumference of the insulating member 47 and the inner circumference of the camera housing 34. A connector receptacle that is annularly (shaped like a doughnut) mounted on the imaging optical system housing 35 is sealed hermetically to permit autoclaving and is thus structured to be watertight. The watertight structure is durable to autoclaving. Although steam will come in and out of the watertight structure during autoclaving, the watertight structure is nevertheless durable to the high temperature and high pressure of the steam. Moreover, watertightness against liquids such as ordinary chemicals is preserved.

Iris driving signal harnesses 50 are joined with the contact pins 49. An anti-breaking member 51 for preventing breaking of the camera cable 18 is located at the back end of the camera housing 34. The anti-breaking member is formed with an elastic member that attains watertightness relative to the camera cable 18.

According to the imaging assembly 5 for endoscopes having the foregoing structure, the electric optical adapter unit 3 is hermetic enough to withstand autoclaving. The imaging optical system in the center of the TV camera unit 4 is also hermetic enough to withstand autoclaving. The connector receptacle mounted on the imaging optical system can transfer or relay an electrical signal to or from the connector of the electric optical adapter unit 3 having a hermetic structure.

Since the TV camera unit and electric optical adapter unit can be separated from each other, the electric optical adapter unit 3 or TV camera unit 4 can be replaced freely with another. Thus, an electric optical adapter unit or TV camera unit having different characteristics can be used in combination. A proper electric adapter unit and TV camera unit can be used in combination according to a use environment in which an endoscopic examination is conducted. This enables easy expansion of the capability of the endoscope system. For example, when a high resolution is required, a TV camera unit 4 having a CCD 40 which permits a large number of pixels to be displayed would be used in combination with the electric optical adapter unit 3.

Moreover, the center of the electric optical adapter unit 3 is designed as an optical path and is surrounded with the contact pins 29. This results in the small outer diameter of the electric optical adapter unit 3. Moreover, the imaging optical system is hermetically sealed to withstand autoclaving and is located in the center of the TV camera unit 4. The contact sockets 48 are also structured hermetically to withstand autoclaving and are freely detachably attached to the contact pins 29 of the electric optical adapter unit 3 and mounted on the circumference of the imaging optical system. This contributes to the small outer diameter of the TV camera unit.

Structures shown in FIGS. 4A and 4B may be adopted as variants of the receptacle 36. In FIG. 2, the receptacle 36 is provided independently of the imaging optical system housing 35. In FIG. 4A, the receptacle is united with the imaging optical system housing 35. Through-holes are bored in the imaging optical system housing 35, and contact sockets 52 are fitted hermetically using glass hermetic seals 53.

In this case, contact pin insertion holes extending from both ends of each contact socket are blocked with a center wall.

Even in FIG. 4B, the receptacle 36 shown in FIG. 2 is united with the imaging optical system housing 35. Through-holes are bored in the imaging optical system housing 35. Contact sockets 54 having contact pin insertion holes into which the contact pins 29 are inserted, extend from the front end thereof and are fitted hermetically using glass hermetic seals 56. Contact pins 55 extend from the back ends of the contact sockets.

The operation and advantages of the variants are nearly identical to those of the first embodiment.

Figure 5:
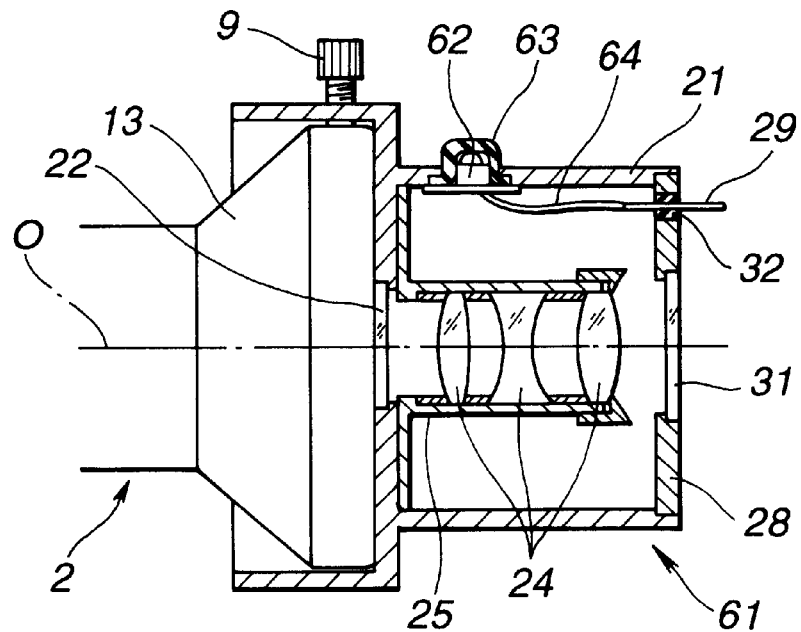
FIG. 5 is a sectional view showing a structure of an electric optical adapter unit in the second embodiment of the present invention.

FIG. 5 shows an electrical optical adapter unit 61 in a second embodiment of the present invention. In describing the electric optical adapter unit 61, the aperture blades 23 and iris drive unit 26, shown in FIG. 2, are excluded from the adapter housing 21 in FIG. 5. A hole is bored at a right position in the top of the outer circumference of the adapter housing 21. A switching contact is fitted in the hole, and a substrate having a remote switch 62 is mounted hermetically on the inner circumferential wall of the hole. The switching contact is shielded so as to be watertight with a rubber cover 63 shaped like a sack and durable to a high temperature. When the outer side of the rubber cover 63 is pressed, the switching contact is turned on.

A pattern conducting electricity to the switching contact is formed on the back surface of the substrate having the remote switch 62. A remote switch harness 64 having one end thereof coupled to the pattern is joined with the contact pin 29 penetrating through the first plug 28.

The electric optical adapter unit 61 is electrically coupled to the CCU 7 via the TV camera unit 4 shown in FIG. 1. The remote switch 62 can be used as a freeze switch for instructing the CCU 7 to display a still image or as a release switch for instructing recording of an image when an image recording apparatus that is not shown is connected.

The operation of this embodiment is nearly identical to that of the first embodiment except that the capability of an electrical circuit is different from that in the first embodiment. Moreover, the advantages of this embodiment are also nearly identical to those of the first embodiment.

Figure 6:
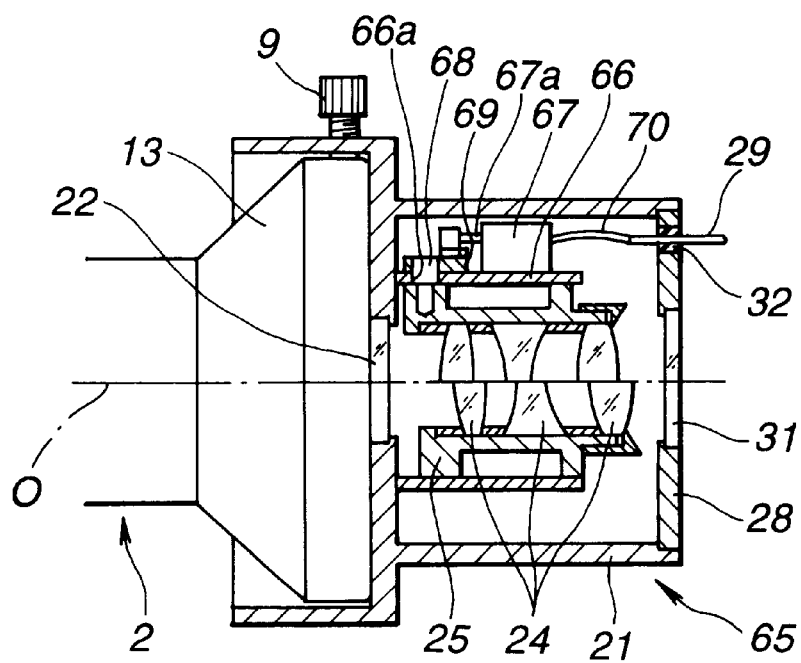
FIG. 6 is a sectional view showing a structure of an electric optical adapter unit in the third embodiment of the present invention.

FIG. 6 shows an electric optical adapter unit 65 in a third embodiment of the present invention. In describing the electric optical adapter unit 65, the aperture blades 23 and iris drive unit 26 shown in FIG. 2 are excluded from the adapter housing 21 in FIG. 6. The lens frame 25 is placed on a locking frame 66 located on the outer circumference of the lens frame 25 so that the lens frame 25 can slide freely. A focus drive unit 67 is mounted on the locking frame 66.

A pin 68 is thrust through the lens frame 25. The pin 68 penetrates through a spiral groove 66a of the locking frame 66, and extends through the outer circumference of the locking frame 66. The pin 68 is attached to a movable member 69. The movable member 69 is provided with a gear. The gear is engaged with a gear that is attached to a rotation shaft 67a of a motor forming the focus drive unit 67.

When the motor is rotated, the movable member 69 rotates. With the rotation, the pin 68 moves in the spiral groove 66a. The lens frame 25 moves in the direction of an optical axis O. This enables the user to vary the focus setting. The other end of a focus driving harness 70 having one end thereof coupled to the focus drive unit 67 is joined with the contact pin 29.

The operation of this embodiment is nearly identical to that of the first embodiment except that the capability of the electrical circuit is different. Moreover, the advantages of this embodiment are also nearly identical to those of the first embodiment.

Figure 7:
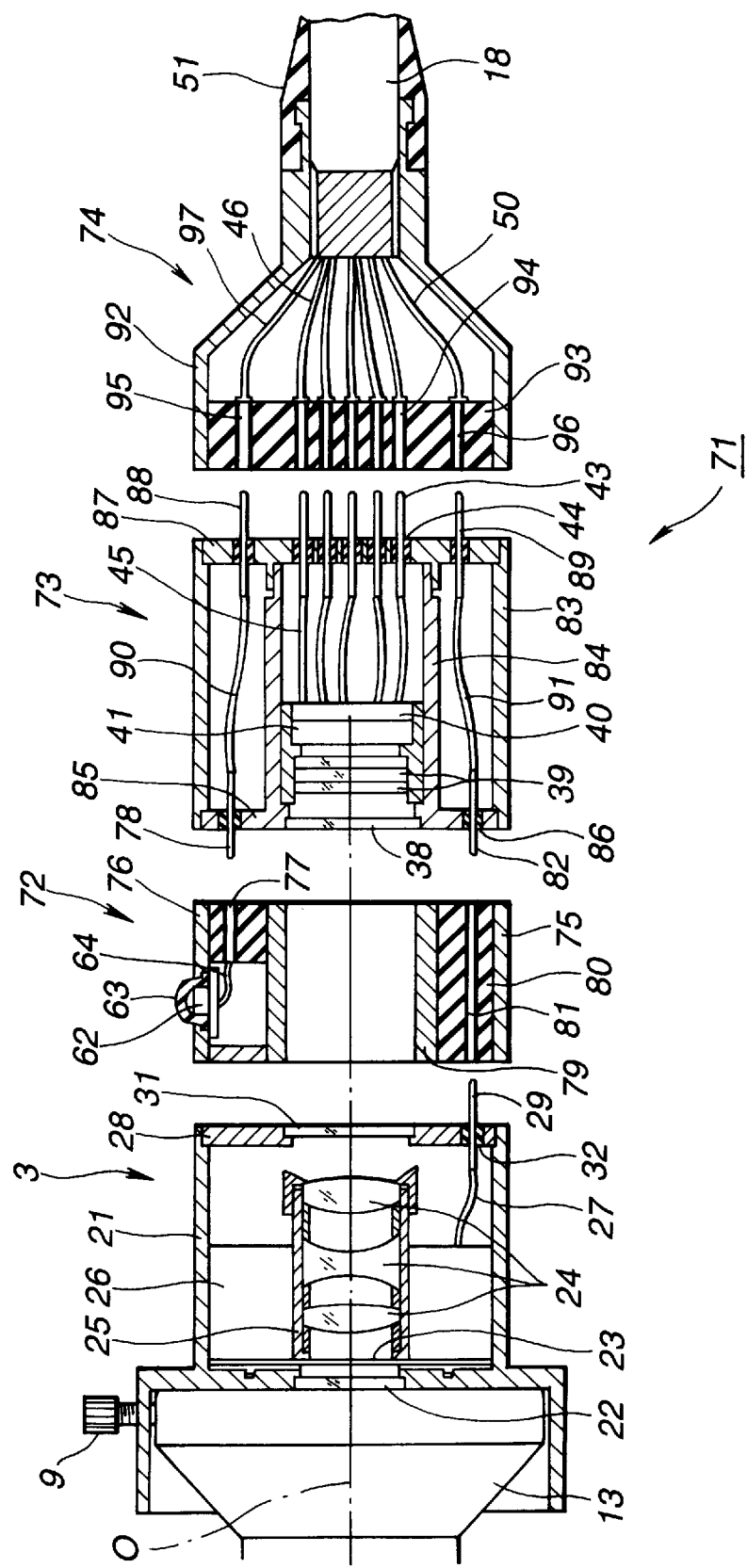
FIG. 7 is a sectional view of a structure of an imaging assembly for endoscopes in accordance with the fourth embodiment of the present invention.

FIG. 7 shows an imaging assembly 71 for endoscopes in accordance with a fourth embodiment of the present invention. The imaging assembly 71 for endoscopes comprises the electric optical adapter unit 3 shown in FIG. 2, a remote switch unit 72, a camera head unit 73, and a cable unit 74.

According to this embodiment, the TV camera unit 4 included in the imaging assembly 5 for endoscopes shown in FIG. 2 is divided into two portions that are the camera head unit 73 and cable unit 74. The remote switch unit 72 is interposed between the electric optical adapter unit 3 and camera unit 73.

The remote switch unit 72 is freely detachably attached to the electric optical adapter unit 3. The remote switch unit 72 has the remote switch 62 mounted hermetically on the outer circumference of a cylindrical remote switch housing 75 in the same manner as the one shown in FIG. 5.

The remote switch 62 is connected to a contact socket 77 of a receptacle 76 located at the back end of the remote switch housing 75. A contact pin 78 of the camera head unit 73 is freely detachably attached to the contact socket 77.

Moreover, a cylindrical frame 79 is placed in the center of the remote switch unit 72 in which the cylindrical frame is opposed to the cover glass 31. The hollow portion of the cylindrical frame 79 forms an optical path leading to an imaging optical system in the camera head unit 73 connected to the back end of the remote switch unit 72.

Moreover, a receptacle 80 is located at a position at which the receptacle is opposed to the contact pins 29 of the electric optical adapter unit 3. The contact pins 29 are fitted in the front portions of the contact sockets 81 bored in the receptacle 80. Contact pins 82 of the camera head unit 73 are freely detachably attached to the back portions of the contact sockets 81 in the remote switch unit 72.

The camera head unit 73 has an imaging optical system housing 84 locked hermetically in a camera housing 83. The camera housing 83 is shaped like a cylinder. The rim of a plug 85 formed like a flange as part of the plug is fixed hermetically to the front end of the imaging optical system housing 84 in the front-end circular opening of the camera housing 83.

The cover glass 38 is mounted hermetically in the face of the imaging optical system housing 84 in the same manner as that for the camera head 17 shown in FIG. 2. The optical filter 39 and CCD 40 are sealed in the imaging optical system housing 84 with the device frame 41 between them.

Moreover, the contact pins 78 and 82 are fitted hermetically in the plug 85 on the face of the imaging optical system housing 84 by means of glass hermetic seals 86.

Moreover, a plug 87 is locked hermetically in a back-end circular opening of the camera housing 83. Contact pins 43 joined with video signal harnesses 45 extending form the CCD 40 are locked hermetically around the center of the plug 87 by means of glass hermetic seals 44. Contact pins 88 and 89 are locked hermetically at outer circumferential positions in the plug 87 by means of glass hermetic seals.

The contact pin 88 is linked to the contact pin 78 by a remote switch harness 90. The contact pins 89 are linked to the contact pins 82 by iris driving harnesses 91.

On the other hand, the cable unit 74 has the back end of a connector housing 92 thereof attached to the front end of the camera cable 18. A receptacle 93 is fitted in a circular opening at the front end of the connector housing 92. Contact socket 94 into which the contact pins 43 are fitted are bored near the center of the receptacle 93. Contact sockets 95 and 96 into which the contact pins 88 and 89 are fitted are bored around the contact sockets 94.

Moreover, the back ends of the contact sockets 94 are joined with video signal harnesses 46 extending from the camera cable 18. The back end of the contact socket 95 is joined with a remote switch harness 97. The back ends of the contact sockets 96 are joined with iris driving harnesses 50. The other components are identical to those described with reference to FIG. 2.

According to this embodiment, the camera head unit 73 may be replaced with another having different characteristics. Any camera head unit having different characteristics can be used in combination. Iris control or display of a still image which is enabled by the remote switch unit 72 can be effected in combination if necessary or according to a use environment. The imaging assembly for endoscopes can therefore be adapted to a wide range of different use environments. Other advantages are nearly identical to those of the first embodiment.

Figure 8:
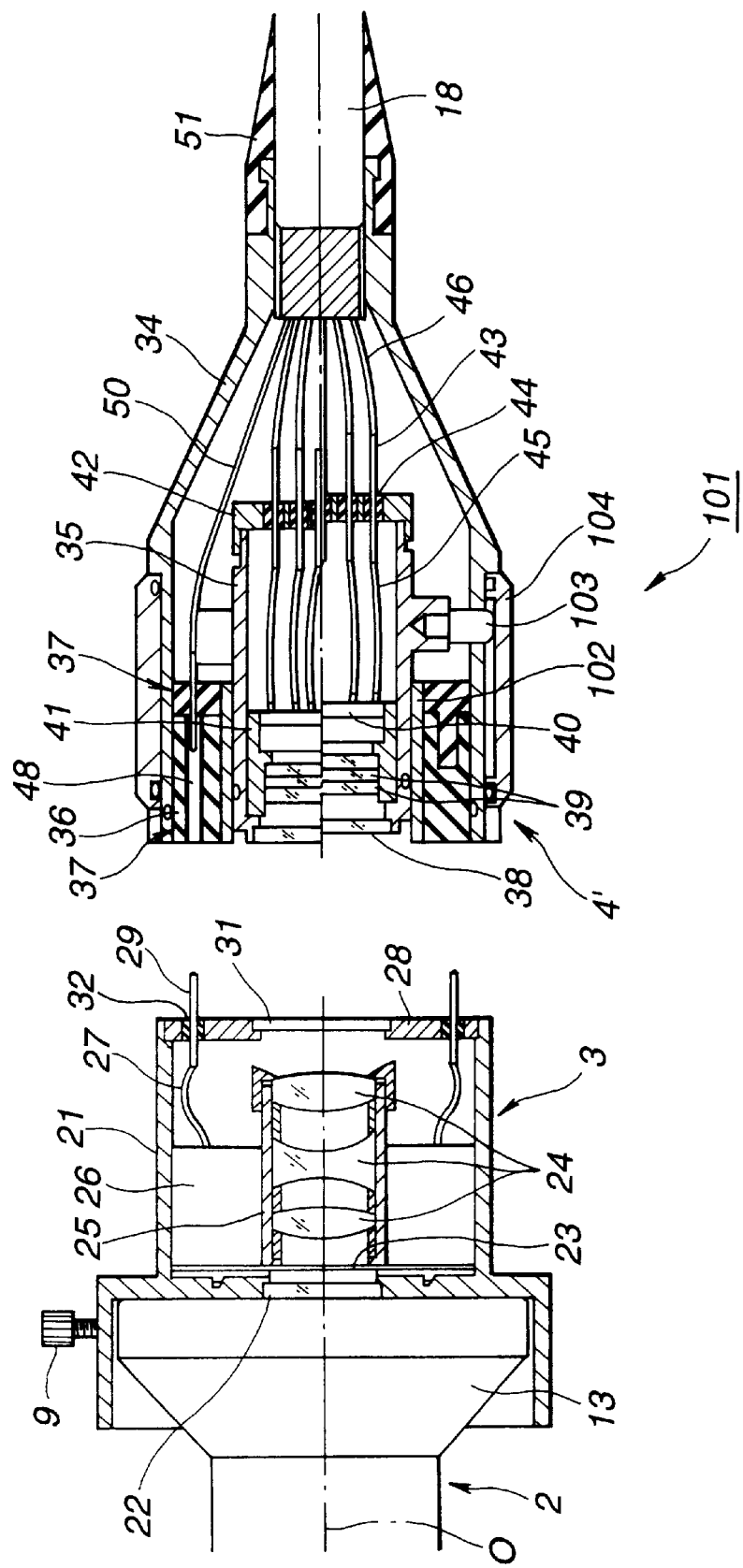
FIG. 8 is a sectional view showing a structure of an imaging assembly for endoscopes in accordance with the fifth embodiment of the present invention.

FIG. 8 shows an imaging assembly for endoscopes 101 in accordance with a fifth embodiment of the present invention. In the imaging assembly for endoscope 101, the TV camera unit 4 included in the imaging assembly for endoscopes 5 shown in FIG. 2 is remodeled into a TV camera unit 4'. The TV camera unit 4' is structured to be focused by moving the imaging optical system housing 35, which is hermetically structured and sealed in the TV camera unit 4, in the direction of the optical axis O.

To be more specific, the imaging optical system housing 35 is placed in an inner cylindrical member 102 of the camera housing 34 so that the imaging optical system housing 35 can slide freely. A pin 103 is thrust through the imaging optical system housing 35. The pin 103 penetrates through a spiral groove of the camera housing 34 and fitted in a groove elongated in the direction of the axis of a focus ring 104.

When the focus ring 104 is turned, the imaging optical system housing 35 is moved spirally together with the pin 103. Thus, a focusing function may be achieved.

An O-ring useful in attaining watertightness is interposed between positions near both ends of the focus ring 104 and the camera housing 34 which are slid relative to each other, and between the imaging optical system housing 35 and the camera housing 34 which are slid relative to each other. A connector receptacle mounted on the outer circumference of the imaging optical system housing 35 is also structured to be watertight.

Other components are nearly identical to those of the imaging assembly for endoscopes 5 shown in FIG. 2. The description of those components will be omitted.

According to this embodiment, an annular connector receptacle 36 transmits an electric signal. The receptacle 36 is structured to allow an optical system to slide on the inner circumference thereof. This results in a small outer diameter of the receptacle.

Moreover, since the hermetically sealed sliding frame is structured as one unit, a simple sliding structure can be realized which is both inexpensive and reliable.

In short, the imaging assembly for endoscope 5 in accordance with the first embodiment is upgraded to enable focusing. Operation of this embodiment and the other advantages thereof are identical to those of the first embodiment.

Figure 9:
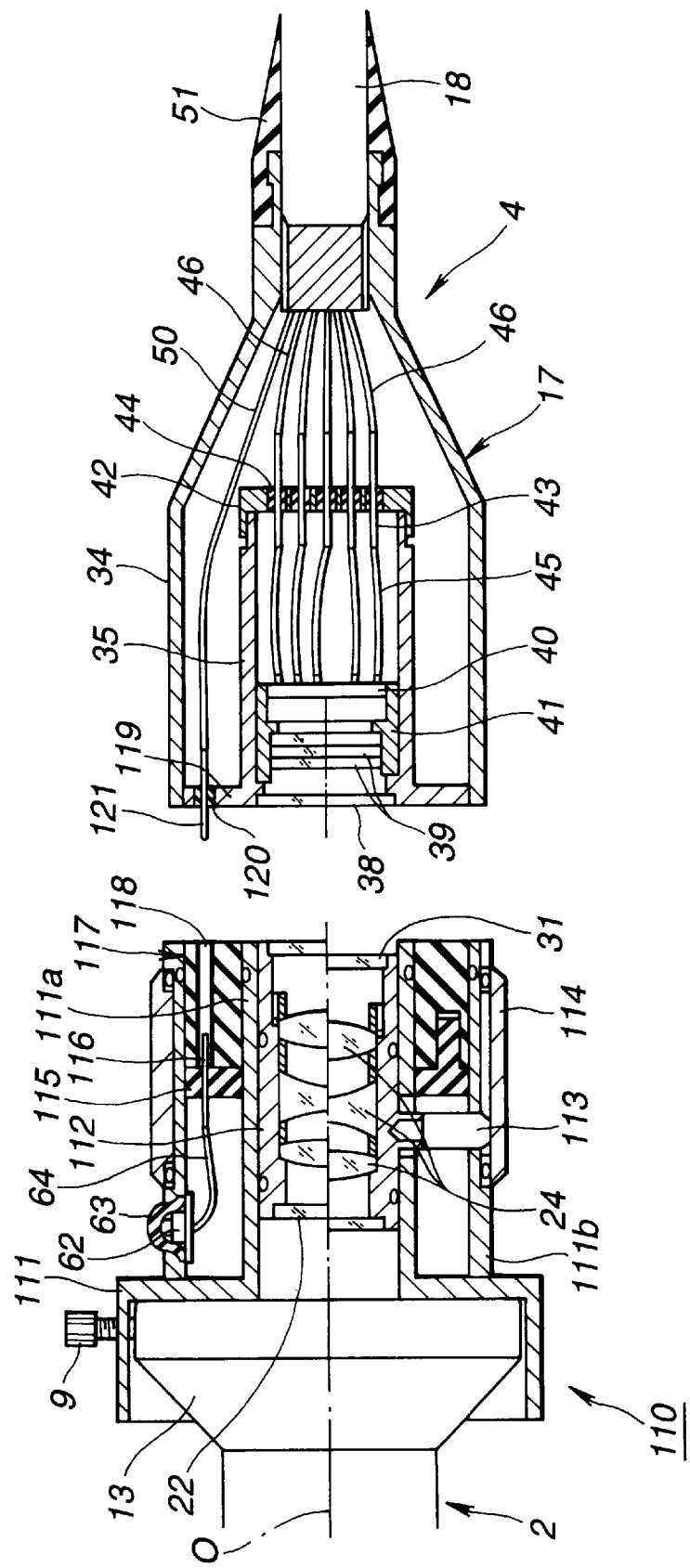
FIG. 9 is a sectional view showing a structure of an imaging assembly for endoscopes in accordance with the sixth embodiment of the present invention.

FIG. 9 shows an imaging assembly for endoscopes 110 in accordance with a sixth embodiment. In FIG. 8, the TV camera unit 4 is provided with a manual focusing means. In this embodiment, the manual focusing means is included in the electric optical adapter unit 3. Moreover, the electric optical adapter unit 3 is provided with the remote switch 62 serving as an electrical circuit.

The back portion of a camera housing 111 having a mount attached to the front end thereof has a smaller diameter. An inner cylindrical portion 111a is formed. A lens frame 112 is disposed in the inner cylindrical portion so that the lens frame can slide freely. The cover glass 22 is hermetically fitted in a circular opening at the front end of the lens frame 112. The system of image formation lenses 24 is placed inside the cover glass. The cover glass 31 is fitted hermetically in a circular opening at the back end of the lens frame. The optical system portion is structured to be hermetically sealed to withstand autoclaving.

A pin 113 is thrust through the lens frame 112. The pin 113 penetrates through a spiral groove in the inner cylindrical portion 111a on the outer circumference of the lens frame 112. The pin 113 further penetrates through a spiral groove in an outer cylindrical portion 111b. The outer cylindrical portion 111b is located on the side of the outer circumference of the inner cylindrical portion 111a and has the front end thereof fixed hermetically to the camera housing 111. The pin 113 is then fitted in a groove elongated in the direction of the axis of the focus ring 114.

When the focus ring 114 is turned, the pin 113 turns along the elongated groove in the outer cylindrical portion 111b. The lens frame 112 turns along the elongated groove together with the pin 113. Thus, focus is achieved.

Moreover, the remote switch 62 is mounted hermetically at a position on the top of the outer cylindrical portion 111b adjacent to the focus ring 114. The remote switch harness 64 is extending from the back surface of the substrate having the remote switch 62. The remote switch harness 64 is joined with the front end of a contact pin 116 thrust through a plug 115 fitted in an annular space between the inner cylindrical portion 111a and outer cylindrical portion 111b.

The back end of the contact pin 116 is fitted in a contact socket 118 bored in a receptacle 117 adjoining the plug 115.

A contact pin 121 hermetically is fitted in a plug 119 at the front end of the camera head 17 using a glass hermetic seal 120. Contact pin 121 is then fitted into the contact socket 118 to meet with contact pin 116, which causes the contact socket 118 to become electrically conductive.

Moreover, a seal member such as an O-ring is interposed between the inner circumferential positions at both ends of the focus ring 114 and the outer circumference of the outer cylindrical portion 111b, between the inner circumference of the outer cylindrical portion 111b and the outer circumference of the receptacle 117, and between the inner circumference of the receptacle 117 and the outer circumference of the inner cylindrical portion 111a. Thus, the connector portion (around the hermetically sealed optical system portion) is structured to be watertight.

The other components are identical to those of the first embodiment. According to this embodiment, the same advantages as those of the fifth embodiment are exerted.

Specifically, the imaging assembly for endoscopes 5 in accordance with the first embodiment is upgraded to be capable of being focused. The operation of this embodiment and the other advantages thereof are identical to those of the first embodiment.

FIG. 10 shows an imaging assembly for endoscopes 131 in accordance with a seventh embodiment. For this embodiment, the TV camera unit 4 included in the imaging assembly for endoscopes 5 shown in FIG. 2 is divided into a filter unit 132 and a main TV camera unit 133.

Circular openings at both ends of the center of a filter housing 134 outlining the filter unit 132 are sealed hermetically with cover glasses 135 and 136 respectively. An optical low-pass filter 137 is sealed inside the cover glasses.

Contact sockets 138 are located at positions along the outer circumference of the filter housing 134 at which the contact sockets are opposed to the contact pins 29.

On the other hand, an imaging optical system housing 142 is stowed in the center of a main TV camera unit housing 141 outlining the main TV camera unit 133. A front-end opening of the imaging optical system housing 142 is sealed hermetically with the cover glass 38. The CCD 40 is located in the imaging optical system housing 142 with the device frame 41 between them.

Moreover, the front end of the imaging optical system housing 142 is extended like a flange. A plug 143 is thus formed by the flange. Contact pins 144 are sealed at positions opposed to the contact sockets 138 by means of glass hermetic seals 145.

The contact pins 144 are joined with iris driving harnesses 50. The other components are identical to those described in conjunction with FIG. 2. The description of the components will be omitted.

According to this embodiment, filter unit 132 including an optical low-pass filter 137 which exhibits characteristics suitable for the number of pixels permitted by the CCD 4 employed in the main TV camera unit 133 can be used in combination therewith. Even when the CCD 4 permits a different number of pixels, occurrence of noises causing aliasing can be effectively prevented. A good-quality image can thus be produced. Other advantages of this embodiment and the operation thereof are identical to those of the first embodiment.

FIG. 11 shows a filter unit 150 in accordance with a variant of the seventh embodiment.

In describing the filter unit 150, the filter unit 132 shown in FIG. 10 is restructured so that a filter unit 151 including the center optical system and a receptacle unit 152 to which the filter unit 151 can be freely detachably attached can be separated from each other freely.

Specifically, the filter unit 151 has circular openings at both ends thereof sealed hermetically with cover glasses 135 and 136 respectively. An optical low-pass filter 137 is sealed inside the cover glasses. The outer circumference of the filter unit 151 is threaded. On the other hand, the receptacle unit 152 formed with an insulating member is provided with contact sockets 138. The center of the receptacle unit 152 is hollowed, and the inner circumference thereof is threaded. The threaded portions are engaged with each other.

According to this variant, the receptacle unit 152 is kept while the filter unit 151 is replaced with another if necessary. This leads to a reduction in replacement costs. Other advantages of this variant are identical to those of the seventh embodiment.

Figure 12:
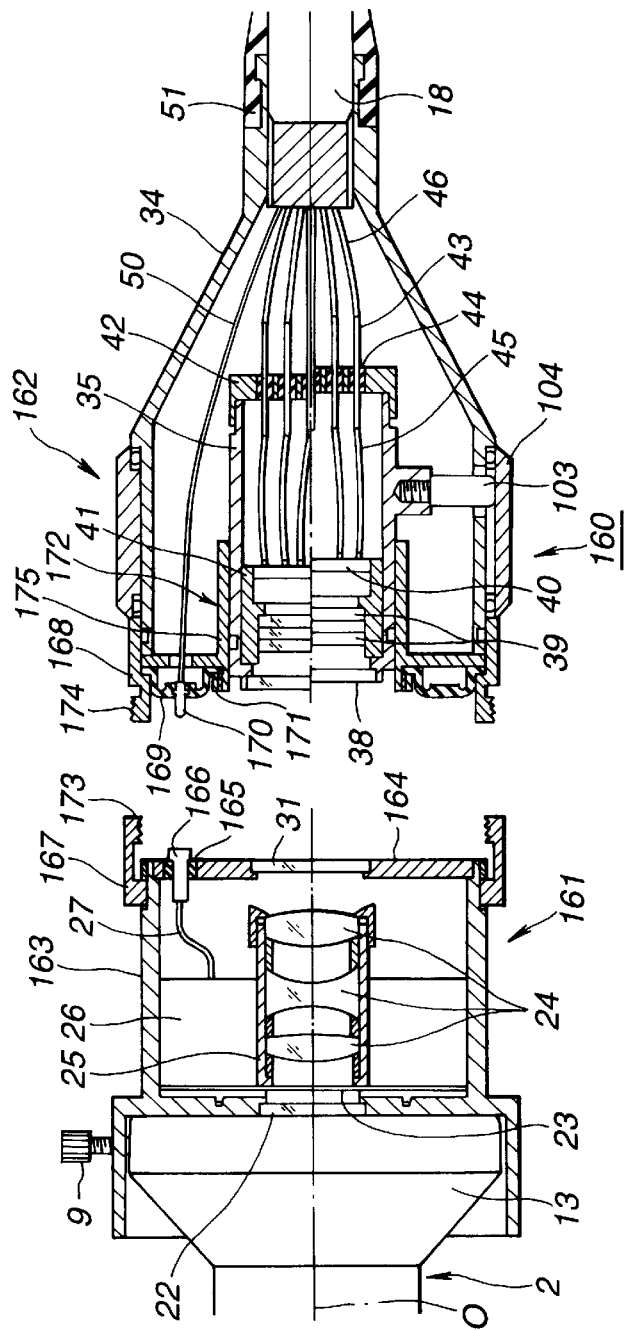
FIGS. 12 and 13 relate to the eighth embodiment of the present invention.

FIG. 12 shows an imaging assembly for endoscopes 160 in accordance with an eighth embodiment of the present invention. In this embodiment, the receptacle 36 of the TV camera unit 4' and the connector of the plug 28 of the electric optical adapter unit 3, which are included in the imaging assembly for endoscopes 101 shown in FIG. 8, are re-structured.

Specifically, a first plug unit 164 shaped like a disk is hermetically sealed on the outer circumference of the back end of a cylindrical adapter housing 163 outlining the electric optical adapter unit 161. A cover glass 31 is sealed hermetically in a circular opening in the center of the first plug unit 164. A plurality of first contact pins 166 are hermetically affixed through the annular first plug unit 164 around the cover glass 31 by means of glass hermetic seals 165.

Moreover, a connection ring 167 having a threaded portion 173 is attached to a small-diameter portion of the cylindrical adapter housing 163 near the back end thereof so that the connection ring 167 can pivot freely.

On the other hand, the cylindrical imaging optical system housing 35 is stowed in the center of the camera housing 34 outlining a TV camera unit 162. The imaging optical system housing 35 is structured so that it can slide back and forth in the direction of the optical axis thereof relative to a second plug unit 172 having a cylindrical portion whose inner circumference engages with the outer circumference of the imaging optical system housing 35.

A plug body 175 forming the second plug unit 172 has an annular flange formed near the front end of the cylindrical portion thereof. An annular elastic member 169 is placed to be opposed to the front face of the flange. The outer circumferential portion of the elastic member 169 is clamped between the flange of the plug body 175 and a mount 168 which has a threaded portion 174 capable of being engaged with the connection ring 167. The inner circumferential portion of the elastic member 169 is also clamped between a locking ring 171 and the flange of the plug body 175. Thus, the ability to attain waterproofness is provided.

Second contact pins 170 are located at positions opposed to the first contact pins 166 of the electric optical adapter unit 161. The second contact pins 170 are molded into the elastic member 169 so that they can jut outside and inside the elastic member 169. Harnesses 50 for power supply and signal transmission are joined with the second contact pins 170 through round holes in the plug body 175.

The connection ring 167 of the adapter unit 161 and the mount 168 of the TV camera unit 162 are screwed together and thus joined with each other. The first contact pins 166 and second contact pins 170 are pressed against each other and thus secured due to elastic force exerted by the elastic member 169. Electrical conduction is thus achieved. The other components are identical to those of the fifth embodiment. Hence, description of those components will be omitted.

According to this embodiment, the lengths in the direction of the optical axis of the contact pins 166 and 170 can be reduced. This is effective in preventing deformation of the contact pins 166 and 170. Moreover, the magnitudes by which the contact pins 166 and 170 project outward from the outer surfaces are minimized, so that the outer surfaces can be made flatter. This provides the advantage of preventing adhesion of dust or moisture. Even if dust or moisture adheres, it can be wiped off easily and reliably. Other advantages of this embodiment and the operation thereof are identical to those of the fifth embodiment.

Figure 14:
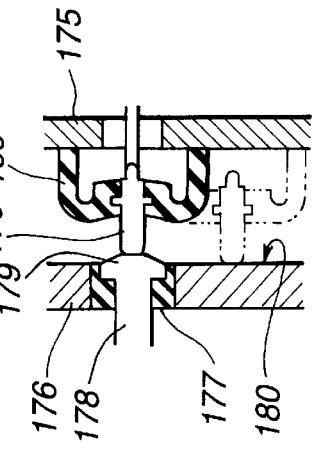
FIG. 14 is a diagram showing an electrically coupled state of the opposed contact pins with connection ring and mount attached to each other in a variant of the eighth embodiment.
Figure 13:
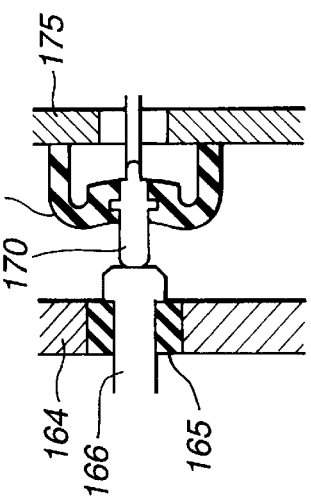

FIG. 14 shows a structure of a connector to be placed between units in accordance with a variant of the eighth embodiment of the present invention. The connector structure is such that first contact pins 178 are fixed hermetically to a first plug unit 176 by means of glass hermetic seals 177 with the first contact pins projecting outside and inside the plug body 176. The first contact pins 178 have tapered heads. The first contact pins 178 are fixed in such a manner that the tapering start lines and the outer surface 180 of the plug body lie substantially on the same plane. The other components are identical to those of the eighth embodiment. Hence, the description of those components will be omitted.

Connection between the electric optical adapter unit 161 and TV camera unit 162 may be attained by rotating them relative to each other with the help of a bayonet joint, which is usually employed between a still camera and a lens unit, or with correspondingly formed threadings on each unit. In this case, the second contact pins 170 rotate near the outer surface 180 of the plug body with the optical axis at the center of rotation, and slide along the tapered surfaces of the heads 179 of the first contact pins 178. The second contact pins 170 are then immobilized with elastic force exerted by the elastic member 169.

According to this variant, whatever method is adopted to connect the electric optical adapter unit 161 and TV camera unit 162 (they may be connected to each other while relatively rotating with the optical axis at the center of rotation or while moving linearly in the direction of the optical axis), the electric contacts thereof conduct reliably. Other advantages of this embodiment and the operation thereof are identical to those of the eighth embodiment.

Incidentally, in the aforesaid embodiments and the like, the optical system in the hermetically sealed body includes at least one of an imaging optical system, a power variation optical system, and an imaging device.

Moreover, any unit having an electric optical system which incorporates therein an electrical circuit for driving an optical system electrically, such as an automatic focus unit, power focus unit, or power zoom unit, may be substituted for the automatic iris unit.

Moreover, embodiments to be constructed by combining or removing parts of the aforesaid embodiments will belong to the present invention.

We claim:

1. An imaging assembly for endoscopes, comprising:
   a first unit to be freely detachably attached to an eyepiece unit of an optical endoscope, said first unit including an optical system located inside said first unit,
      a first housing having a distal first housing opening to oppose an optical device in said eyepiece unit and a proximal first housing opening, and
      an electric circuit which generates an electric signal and is disposed in the first housing, wherein said distal first housing opening is hermetically sealed with a first optical device so that the optical system and electric circuit can withstand autoclaving where high-temperature and high-pressure steam is used for sterilization;
   a second unit including
      an imaging unit which includes a solid-state imaging device for photoelectrically converting an optical image formed through said optical system, and
      a second housing, wherein said imaging unit is sealed hermetically in said second housing, said second housing having a distal second housing opening opposed to said optical system which is sealed hermetically with a second optical device so that the imaging unit can withstand autoclaving;
   a connection member for connecting said first and second units so that they can be easily separated from each other;
   a third optical device which hermetically seals said proximal first housing opening of said first housing;
   a first electric connector having a plurality of first electric contacts hermetically sealed around the circumference of said proximal first housing opening to withstand autoclaving and coupled to said electric circuit; and
   a second electric connector formed around said distal second housing opening and facing said connection member, said second electric connector having a plurality of second electric contacts which are freely detachably attached to said first electric contacts of said first electric connector and having a waterproof structure.

2. An imaging assembly for endoscopes according to claim 1, wherein said plurality of second electric contacts are hermetically sealed around said distal opening of said second housing so that said second electric contacts can withstand autoclaving.

3. An imaging assembly for endoscopes according to claim 2, further comprising a plurality of third electric contacts sealed with hermetic seals around an inner circumference of a proximal end of said second unit, and wherein said second electric contacts are joined with said third electric contacts via signal lines constituting a signal cable.

4. An imaging assembly for endoscopes according to claim 1, wherein said electric circuit is one of an electric optical system unit for electrically driving at least part of said optical system or a remote switch used for remote handling.

5. An imaging assembly for endoscopes according to claim 4, wherein said electric optical system unit is one of an automatic iris unit, an automatic focus unit, a power focus unit, and a power zoom unit.

6. An imaging assembly for endoscopes according to claim 1, wherein said imaging unit includes an optical filter located on a face of said solid-state imaging device.

7. An imaging assembly for endoscopes according to claim 1, wherein said second unit has a cylindrical frame for said second electric connector which is structured to be waterproof and hermetically sealed, and is located coaxially with said imaging unit on the circumference thereof.

8. An imaging assembly for endoscopes according to claim 7, wherein said imaging unit is slidable relative to said frame.

9. An imaging assembly for endoscopes according to claim 8, wherein the combination of said slidable imaging unit and said optical system have at least one of the ability to vary a power of the optical system to focus an optical image formed on said solid-state imaging device or the ability to vary the size of the optical image.

10. An imaging assembly for endoscopes according to claim 1, further comprising a third unit having an optical filter hermetically stowed therein to permit autoclaving, and wherein said third unit is freely detachably attached to said first and second units.

11. An imaging assembly for endoscopes according to claim 1, further comprising a third unit which includes a third electric connector for electrically connecting said first electric contacts of said first electric connector and said second electric contacts of said second electric connector, wherein said third unit is freely detachably attached to said first and second units.

12. An imaging assembly for endoscopes according to claim 1, wherein said first electric contacts are heremetically sealed by cooling and thus solidifying fused glass on the circumferences of said first electric contacts.

13. An imaging assembly for endoscopes according to claim 1, wherein said first, second, and third optical devices are hermetically sealed by soldering or waxing metallically coated portions around the circumferences of said distal first housing opening, said distal second housing opening, and said proximal first housing opening, respectively, so that said first, second, and third optical devices can withstand autoclaving.

14. An imaging assembly for endoscopes according to claim 1, wherein said autoclaving is process of exposing an object to be sterilized to steam having a temperature ranging from 121 to 135° C. and a pressure ranging from 1.5 to 2.2 atm, for a duration from about 5 to 20 min.

15. An imaging assembly for endoscopes, comprising:

a first unit to be freely detachably attached to an eyepiece unit of an optical endoscope, the first unit including
a cylindrical first housing having a proximal opening and a distal opening hermetically sealed with first and second optical devices, respectively, the distal opening of the first housing to be opposed to an optical device in said eyepiece unit,
an optical system located inside the first housing and hermetically sealed between the first and second optical devices so that the optical system can withstand autoclaving where high-temperature and high-pressure steam is used for sterilization;

a second unit including
an imaging unit which includes a solid-state imaging device for photoelectrically converting an optical image formed through said optical system, and
a second housing, wherein said imaging unit is sealed hermetically in said second housing, said second housing having a distal opening opposed to said optical system which is hermetically sealed with a third optical device so that the imaging unit can withstand autoclaving;

a separable connection member for connecting said first and second units so that they can be separated from each other;

a first electric connector having a plurality of first electric contacts which are hermetically sealed around the circumference of the proximal opening of said first housing so that said electric contacts can withstand autoclaving;

a second electric connector formed in said second housing facing said separable connection member and having a plurality of second electric contacts which are freely detachably attached to said first electric contacts of said first electric connector; and a waterproof housing structured to be waterproof for shielding said second electric connector so that said second electric connector can withstand autoclaving.

16. An imaging assembly for endoscopes according to claim 15, further comprising an electric drive unit for electrically driving said optical system in said first housing.

* * * * *